United States Patent
Meah

(10) Patent No.: US 10,912,622 B2
(45) Date of Patent: Feb. 9, 2021

(54) DISPOSABLE ENDOSCOPE SHIELD

(71) Applicant: Nizam M. Meah, Manvel, TX (US)

(72) Inventor: Nizam M. Meah, Manvel, TX (US)

( * ) Notice: Subject to any disclaimer, the term of this patent is extended or adjusted under 35 U.S.C. 154(b) by 0 days.

(21) Appl. No.: 16/428,965

(22) Filed: Jun. 1, 2019

(65) Prior Publication Data

US 2020/0375684 A1 Dec. 3, 2020

(51) Int. Cl.
*A61B 46/00* (2016.01)
*A61B 46/23* (2016.01)
*A61B 17/00* (2006.01)
*A61B 46/20* (2016.01)

(52) U.S. Cl.
CPC .............. *A61B 46/30* (2016.02); *A61B 46/23* (2016.02); *A61B 2017/0023* (2013.01); *A61B 2046/205* (2016.02)

(58) Field of Classification Search
CPC ..... A61B 46/30; A61B 90/05; A61B 1/00142; A61B 1/31; A61B 46/10; A61B 46/20
See application file for complete search history.

(56) References Cited

U.S. PATENT DOCUMENTS

| | | | |
|---|---|---|---|
| 3,286,713 A * | 11/1966 | Kurtz | A61F 13/00021 604/180 |
| 3,417,746 A * | 12/1968 | Moore | A61B 1/2676 600/184 |
| 3,813,092 A * | 5/1974 | Foster | A61M 16/009 5/600 |
| 3,921,635 A * | 11/1975 | Gauthier | A61M 3/025 604/84 |
| 4,043,328 A * | 8/1977 | Cawood, Jr. | A61B 42/00 128/850 |
| 4,445,898 A * | 5/1984 | Jensen | A61F 5/441 604/332 |
| 4,570,628 A * | 2/1986 | Neal | A61B 46/30 128/853 |
| 4,834,068 A * | 5/1989 | Gottesman | A61B 1/00142 128/846 |
| 4,848,322 A * | 7/1989 | Dash | A61B 90/05 600/119 |
| 4,976,254 A * | 12/1990 | Dash | A61B 90/05 128/857 |
| 5,024,212 A * | 6/1991 | Bonnet | A61B 90/05 600/105 |

(Continued)

*Primary Examiner* — Timothy J Neal
*Assistant Examiner* — Jae Woo
(74) *Attorney, Agent, or Firm* — Kanika Radhakrishnan; Evergreen Valley Law Group

(57) ABSTRACT

The present disclosure provides a disposable endoscope shield including a shield body member having a first surface configured to cover a treatment area of a subject and a second surface oriented towards a user of an endoscope device. The shield body member is configured with an opening extending from the first surface to the second surface for allowing the endoscope device to access an internal organ of the subject via a cavity, for performing an endoscopy. A fluid protection layer is configured between the first surface and the second surface of the shield body member, for protecting the user from fluids splattering from the internal organ of the subject during the endoscopy. The shield also includes a pocket member and is configured to a medical procedure mat.

17 Claims, 7 Drawing Sheets

(56) References Cited

U.S. PATENT DOCUMENTS

| Patent/Pub No. | | Date | Inventor | Classification |
|---|---|---|---|---|
| 5,062,840 | A * | 11/1991 | Holt | A61F 13/495 604/385.19 |
| 5,123,402 | A * | 6/1992 | Vandenbossche | A61B 90/05 128/857 |
| 5,224,940 | A * | 7/1993 | Dann | A61B 90/05 604/187 |
| 5,305,765 | A * | 4/1994 | Potts | A61F 13/00 128/849 |
| 5,395,354 | A * | 3/1995 | Vancaillie | A61B 1/12 128/846 |
| 5,496,290 | A * | 3/1996 | Ackerman | A61M 3/0279 433/116 |
| 5,522,403 | A * | 6/1996 | Bark | A61B 46/00 128/849 |
| 5,554,111 | A * | 9/1996 | Morrey | A61F 2/4675 433/29 |
| 5,594,789 | A | 1/1997 | Seazholtz et al. | |
| 5,665,073 | A * | 9/1997 | Bulow | A61M 25/02 604/263 |
| 5,697,887 | A * | 12/1997 | Yabe | A61B 1/00142 600/121 |
| 5,921,917 | A * | 7/1999 | Barthel | A61B 1/07 128/200.26 |
| 5,960,794 | A * | 10/1999 | Shaw | A61B 46/30 128/849 |
| 6,050,981 | A * | 4/2000 | Lampropoulos | A61M 3/0262 128/849 |
| 6,093,182 | A * | 7/2000 | Lampropoulos | A61M 3/02 604/246 |
| 6,197,010 | B1 * | 3/2001 | Leise, Jr. | A61F 5/443 604/338 |
| 6,357,445 | B1 * | 3/2002 | Shaw | A61B 46/30 128/849 |
| 7,179,247 | B2 * | 2/2007 | Mizutani | A61F 13/47209 600/574 |
| 7,981,026 | B2 * | 7/2011 | Small | A61B 50/20 128/849 |
| 9,427,288 | B1 * | 8/2016 | Chenger | A61B 90/05 |
| 9,901,487 | B2 * | 2/2018 | Steinberg | A61F 13/2011 |
| 10,182,877 | B2 | 1/2019 | Marshburn | |
| 10,363,113 | B1 * | 7/2019 | Chenger | A61B 90/05 |
| 2003/0004477 | A1 * | 1/2003 | Nielsen | A61F 5/448 604/336 |
| 2003/0204174 | A1 * | 10/2003 | Cisko, Jr. | A61F 5/445 604/338 |
| 2004/0038008 | A1 * | 2/2004 | Levine | A61F 13/45 428/189 |
| 2006/0243285 | A1 * | 11/2006 | Small | A61B 46/30 128/849 |
| 2007/0089753 | A1 * | 4/2007 | Faries, Jr. | A61F 7/0085 128/849 |
| 2008/0262462 | A1 * | 10/2008 | Bar-Or | A61B 1/00142 604/385.03 |
| 2008/0300553 | A1 * | 12/2008 | Irion | A61B 46/10 604/263 |
| 2009/0126741 | A1 * | 5/2009 | Voic | A61B 90/40 128/846 |
| 2010/0024831 | A1 * | 2/2010 | Gustafsson | A61B 46/00 128/849 |
| 2010/0249709 | A1 * | 9/2010 | Fischvogt | A61B 17/3421 604/167.01 |
| 2011/0313370 | A1 * | 12/2011 | Smyth | B29C 66/861 604/263 |
| 2012/0157778 | A1 * | 6/2012 | Wheeler | A61M 5/008 600/201 |
| 2013/0225925 | A1 * | 8/2013 | Kang | A61B 1/00154 600/114 |
| 2014/0007886 | A1 * | 1/2014 | Singh | A61B 46/30 128/854 |

\* cited by examiner

DISPOSABLE ENDOSCOPE SHIELD

TECHNICAL FIELD

The present disclosure relates in general to medical devices, and more particularly, relates to an endoscope shield for protecting a user of an endoscope device, from fluids splattered by a subject during endoscopy.

BACKGROUND

In the recent past, one of the common diagnostic procedures employed by medical practitioners for examining an internal organ of a subject, such as a colon, a stomach and the like, is endoscopy. Endoscopy involves the insertion of an elongated cylindrical tube, called an endoscope, into the internal organ via a cavity of the subject. The internal organ is visually examined by the medical practitioner and thereafter a suitable medication is prescribed. Endoscopy has proliferated recently, due to its non-invasive nature and the ability of the medical practitioner to access intricate areas of the internal organ for diagnosis. Additionally, the endoscopy also minimizes discomfort to the subject during and after the procedure enabling the subject to recuperate rapidly.

During an endoscopic procedure, particularly for internal organs such as the colon or the stomach, the medical practitioner is required to insufflate air into the internal organ for distention, which leads to an enhanced vision for the visual examination. The enhanced vision helps the medical practitioner to access intricate areas of the internal organ for accurate diagnosis and to provide a suitable therapy to the affected areas. However, during the endoscopy procedure, it is a natural tendency or reflex of these internal organs to work against the distention and for expelling the excess pressure exerted during the insufflation. The excess pressure is expelled either by forceful burping or hiccupping in case of the stomach or by forceful bowel movement in case of the colon. In such scenarios, a profuse amount of foul-smelling fluids are expelled from the subject during the endoscopy. The foul-smelling fluids may be at least one of stomach acids, bile, liquid, and solid stool or other potentially infectious gas and body secretions. The body secretions are typically expelled in the form of a forceful spray, which may soil the medical practitioner. Additionally, these body secretions travel a long distance at high speeds, as an example, a human sneeze can travel at a speed of 100 miles per hour and spray about 100,000 germs per sneeze in air. As such, these body secretions may contaminate medical equipment in the vicinity of the subject. The body secretions also tend to live in the air or in the environment for weeks, which may contaminate the treatment area or other subjects in the vicinity. Due to a higher shelf-life, these secretions may also travel around other areas in a medical facility through ventilation systems, thereby affecting other patients in the medical facility, which is undesirable.

Therefore, there is a need for techniques which can overcome one or more limitations stated above, in addition to providing other technical advantages.

SUMMARY

Various embodiments of the present disclosure provide a disposable endoscope shield. The shield includes a shield body member having a first surface configured to cover a treatment area of a subject and a second surface oriented towards a user of an endoscope device. The shield body member is configured with an opening extending from the first surface to the second surface for allowing the endoscope device to access an internal organ of the subject via a cavity, for performing an endoscopy. The shield body member also comprises a fluid protection layer is configured between the first surface and the second surface of the shield body member, for protecting the user from fluids splattered, from the internal organ of the subject during the endoscopy.

In another embodiment of the present disclosure, the disposable endoscope shield is disclosed. The shield includes the shield body member including the first surface configured to cover on the treatment area of the subject and the second surface oriented towards a user of the endoscope device. The shield body member is configured with the opening extending from the first surface to the second surface, for allowing the endoscope device to access the internal organ of the subject via the cavity, for performing the endoscopy. The fluid protection layer is also configured between the first surface and the second surface, for protecting the user from fluids splatted from the internal organ of the subject during the endoscopy. Further, a pocket member is also configured to the shield body member, for storing accessories required for the endoscopy.

In another embodiment of the present disclosure, a medical procedure mat is disclosed. The mat includes a cushion member configured with the disposable endoscope shield. The disposable endoscope shield includes the shield body member comprising the first surface configured with a biocompatible adhesive for covering the treatment area of the subject via the shield body member and the second surface oriented towards a user of the endoscope device. The shield body member is configured with an opening extending from the first surface to the second surface, for allowing the endoscope device to access the internal organ of the subject via the cavity, for performing the endoscopy. A slit extends from the opening to the outer surface of the shield body member. The slit is configured with a fastening mechanism operable to an engaged position in which the slit is closed and to a disengaged position in which the slit is open. In the disengaged position of the fastening member, the shield body member is split into a first portion and a second portion, allowing the user to wrap the shield body member around the endoscope device inserted within the internal organ, such that the opening encircles the endoscope device. In the engaged position of the fastening member, the first portion interlocks with the second portion to form a unitary structure of the shield body member. Further, a coupling member is configured around a perimeter of the opening and oriented parallelly about an axis of the opening for engaging with the endoscope device. The coupling member extends from the second surface towards the first surface and sealingly couples with the endoscope device for protecting the user during the endoscopy. Further, the fluid protection layer is configured between the first surface and the second surface, for preventing splashing of fluids onto the user from the subject during the endoscopy. The mat also includes the pocket member configured to the shield body member, for storing accessories required for the endoscopy.

BRIEF DESCRIPTION OF THE FIGURES

The following detailed description of illustrative embodiments is better understood when read in conjunction with the appended drawings. For the purpose of illustrating the present disclosure, exemplary constructions of the disclosure are shown in the drawings. However, the present disclosure is not limited to a specific device or a tool and instrumentalities disclosed herein. Moreover, those in the art will understand that the drawings are not to scale. Wherever possible, like elements have been indicated by identical numbers.

Figure 1:
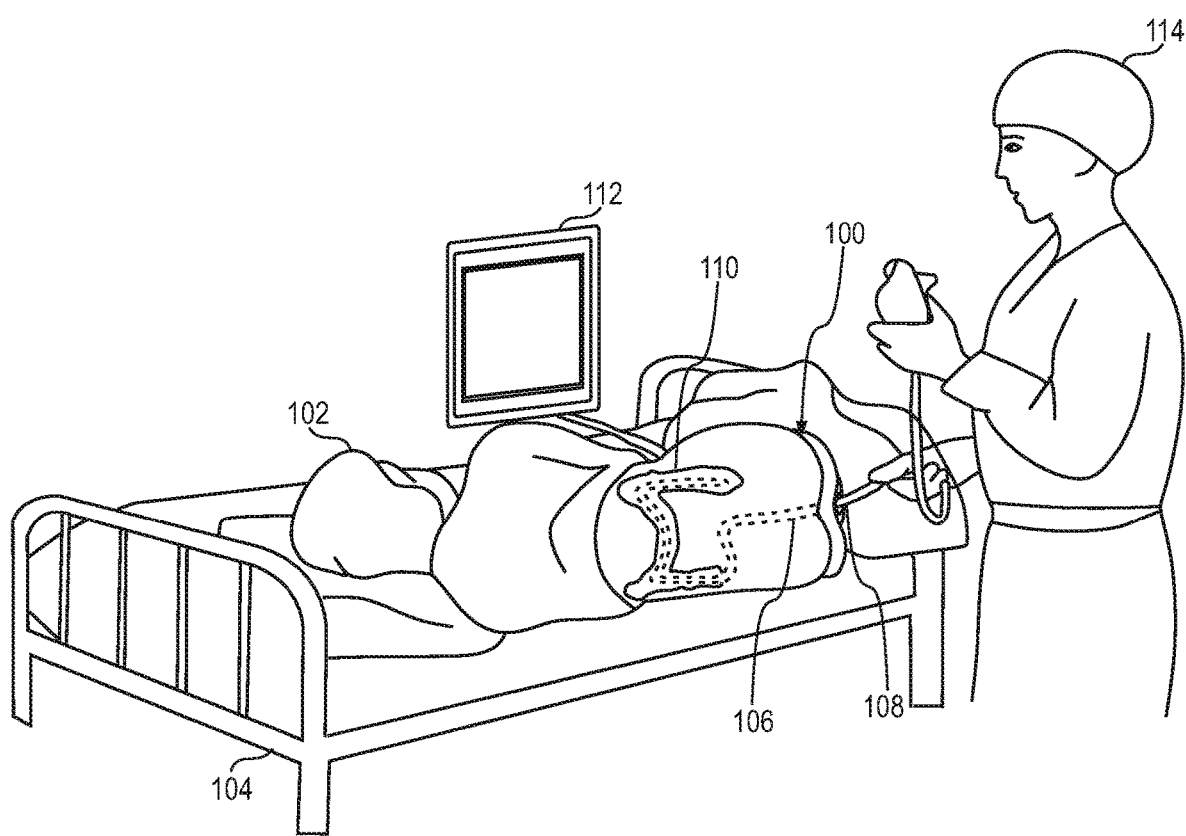
FIG. 1 is a schematic view of a disposable endoscope shield covered on a treatment area of a subject undergoing an endoscopy, in accordance with an exemplary embodiment of the present disclosure.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Reference in this specification to "one embodiment" or "an embodiment" means that a particular feature, structure, or characteristic described in connection with the embodiment is included in at least one embodiment of the present disclosure. The appearance of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

Overview

Various embodiments of the present disclosure provide a disposable endoscope shield. The shield is configured to protect a medical practitioner or a user of an endoscope device from fluids splattering from a subject, during endoscopy. This feature inherently prevents contamination of a treatment area and/or a medical facility in which the subject is undergoing the endoscopy.

The shield includes a shield body member having a first surface and a second surface, wherein the first surface is configured to cover a treatment area of a subject and a second surface is oriented towards a user of the endoscope device. The first surface may also be configured with a biocompatible adhesive, for covering a treatment area of a subject via the shield body member. The second surface is oriented towards the user of an endoscope device or an endoscopist. The shield body member is configured with an opening for allowing the endoscope device to access the internal organ of the subject via the cavity. The opening extends from the first surface to the second surface and is configured to couple with the endoscope to form a leak-proof joint. The opening also acts as a supporting channel to the endoscope which facilitates angular alignment during the endoscopy, while also preventing wobbling. A coupling mechanism may be configured around the perimeter of the opening. The coupling mechanism is configured to sealingly engage with the endoscope inserted into the opening for accessing the internal organ. Also, a bite-block member may be configured to the opening for preventing damage to the endoscope upon insertion.

A fluid protection layer is configured between the first surface and the second surface for protecting the user from fluids splattering during the endoscopy. The fluid protection layer is configured to either absorb or be impervious to the fluids splattered from the internal organ during the endoscopy. This configuration, therefore, acts as a barrier for the fluids splattered by the internal organ during endoscopy, thereby ensuring protection to the user. The shield also includes a pocket member configured to the shield body member. The pocket member may either be extending from the shield member as an integral member or may be fastened to the shield member. The pocket member acts as a storage compartment for storing accessories necessary for the endoscopy.

Further, a slit is configured to the shield body member, which is configured to enable wrapping of the shield around the endoscope. The slit extends from the opening to the outer surface of the shield body member. The slit includes a fastening mechanism operable between an engaged position in which the slit is closed and a disengaged position in which the slit is opened. In the disengaged position the shield body member is split into a first portion and a second portion, for allowing the user to wrap the shield body member around the endoscope device. The shield body member is inserted such that, the opening encircles the endoscope device. In the engaged position, the first portion and the second portion are interlocked to form a unitary structure of the shield body member. This configuration ensures that the shield can be incorporated on the endoscope which is already inserted into the cavity of the subject. Also, this configuration ensures that the shield is interchangeable while performing the endoscopy, in the event the shield gets soiled due to fluids splattering.

The term 'treatment area' used throughout the present disclosure may refer to an area on the subject's body, where the endoscope device can access an internal organ of the subject via a cavity. As such, the treatment area may be one of a mouth region or a buttocks region or any other region on the subject where a cavity can be used by the medication practitioner for accessing the internal organ.

The term 'endoscope' used throughout the present disclosure may typically refer to the endoscope device, which is configured with a slender and tubular instrument used for visual diagnostics of internal organs of the subject. The endoscope may be configured in any shape and configuration as per requirement.

The term 'endoscopy' used throughout the present disclosure may typically refer to a diagnostics procedure employed by medical practitioners by using the endoscope.

The term 'subject' used throughout the present disclosure may refer to a person or an animal on whom the endoscopy is being performed.

The term 'user' or 'medical practitioner' used throughout the present disclosure may refer to a person or an animal who performs the endoscopy on the subject.

Various embodiments of a disposable endoscope shield are explained below in a detailed manner, herein with reference to FIG. 1 to FIG. 9.

FIG. 1 illustrates a schematic representation of an environment including a disposable endoscope shield 100 (hereinafter referred to as shield 100) covered on a treatment area of a subject 102 resting on a medical procedure table 104, in one exemplary embodiment of the present disclosure. The shield 100 may also be attached onto the treatment area of the subject 102. An endoscope 106 is inserted by a user 114 or a medical practitioner 114 into a cavity 108 of the subject 102 and through the shield 100, to access an internal organ 110 for visual diagnosis. As an example, the internal organ 110 may be a colon of the subject 102, and the cavity 108 through which the endoscope 106 accesses the colon may be an anal cavity. The endoscope 106 may be connected to a display device 112 for visual inspection of the internal organ 110 of the subject 102 during the endoscopy. The shield 100 is configured to protect the user 114 of the endoscope 106 from fluids splattered from the subject 102, during endoscopy. This feature inherently prevents contamination of the treatment area and/or a medical facility in which the subject 102 is undergoing the endoscopy.

Figure 2:
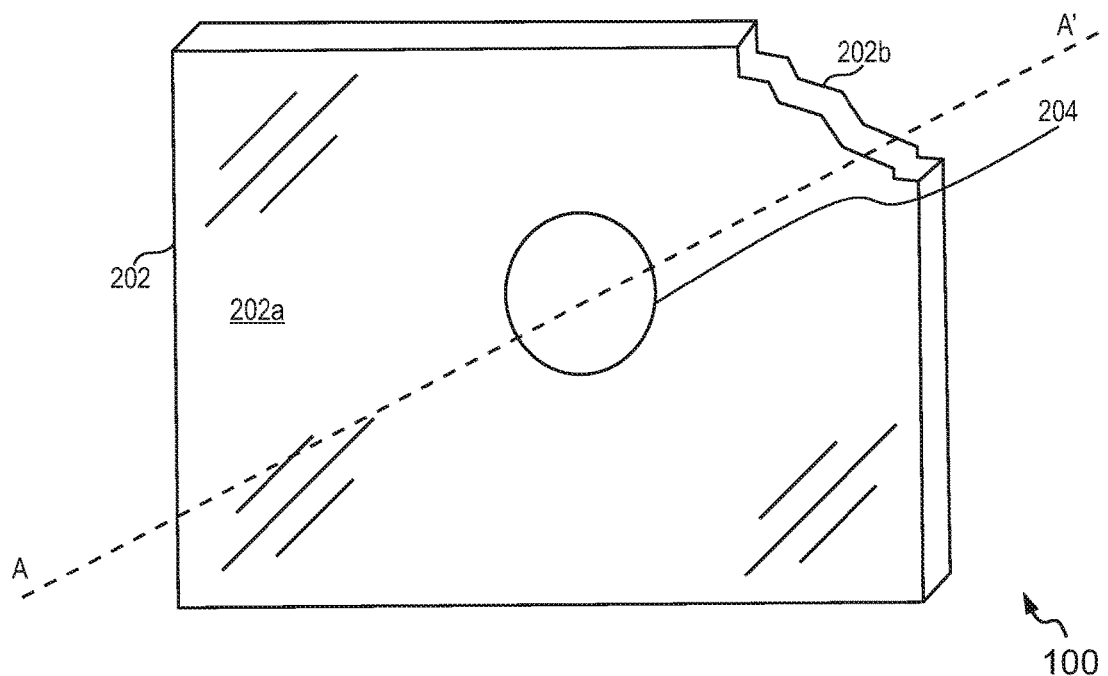
FIG. 2 is a schematic view of the disposable endoscope shield of FIG. 1, in accordance with an exemplary embodiment of the present disclosure.

Referring to FIG. 2 in conjunction with FIG. 1, the shield 100 includes a shield body member 202. The body member 202 defines the perimeter or the boundary of the shield 100 and acts as a frame for the shield 100. The body member 202 may be defined with a predetermined thickness as per the shielding requirements. In one configuration, the thickness of the body member 202 may be in the range of about 5 mm to about 12 cm, as per feasibility and requirement. The body member 202 may also be configured with a predetermined configuration (i.e. shape and dimensions), which may conform to the treatment area to which it would be engaged. The configuration of the body member 202 is selected to provide optimum shielding properties to the fluids splattered from the subject 102. As an example, if the endoscope 106 is inserted into the anal cavity of the subject 102 (for e.g. as shown in FIG. 1) for accessing the colon, the shield 100 may be configured to be rectangular in shape of adequate dimensions for covering the entire buttocks region of the subject 102. In another configuration, the body member 202 may also be configured in shapes such as but not limited to a square shape, a circular shape, an oval shape or any other geometric shape as per design feasibility and requirement.

The body member 202 further includes a first surface 202a and a second surface 202b, wherein the first surface 202a may be configured to cover the treatment area and the second surface 202b is oriented towards the user 114. In one implementation, the first surface 202b includes a biocompatible adhesive layer for attaching the shield 100 on the treatment area. For ensuring attachment of the body member 202, the first surface 202a may be configured with the biocompatible adhesive layer (not shown in Figures). In one configuration, the biocompatible adhesive layer may be a distinct layer which may be secured onto the first surface 202a, for ensuring attachment onto the treatment area of the subject 102 or for covering the treatment area via the body member 202. In another configuration, the biocompatible adhesive layer configured on the first surface 202a is temporary adhesion surface and may be made of natural polymer materials.

The body member 202 is further configured with an opening 204 configured to allow the endoscope 106 to pass therethrough. The opening 204 extends from the first surface 202a to the second surface 202b, along an axis A-A' of the body member 202. The axis A-A' may be a central axis of the body member 202. In one configuration, the axis A-A' may be any axis defined on the body member 202, configured to define the extension or orientation or configuration of the opening 204, as per feasibility and requirement. The opening 204 is typically aligned coaxially with the cavity 108 while covering the treatment area of the subject 102, for allowing the endoscope 106 to access the internal organ 110. The opening 204 conforms with the endoscope 106 to form a leak-proof joint. The configuration of the opening 204 (i.e. the shape and dimension) may establish an interference fit with the outer surface of the endoscope 106. The interference fit prevents misalignment of the endoscope 106 during insertion into the internal organ 110 and during its inspection. thereby acting as a supporting channel for the endoscope 106. The interference fit also enables angular alignment of the endoscope 106 without wobbling, during use on the subject 102. In one configuration, for establishing interference fit with the endoscope 106, the size of the opening 204 is configured to be dimensionally smaller than that of the outer surface of the endoscope 106. However, the dimensions of the opening 204 are selected such that the user 114 is subjected to a minimal hindrance during insertion of the endoscope 106 into the opening 204. In another configuration, the dimensions and configuration of the opening 204 are selected based on the type of engagement with the endoscope 106. Further, the shape of the opening 204 is configured to be identical to the shape of the outer surface of the endoscope 106. In one configuration, the shape of the opening 204 is selected to be one of a circular shape, a square shape, a rectangular shape or any other shape as per design feasibility and requirement.

In one embodiment, the body member 202 may be configured to be folded in multiple orientations and configuration (not shown in Figures), for ease of storing and transportation.

Figure 3A:
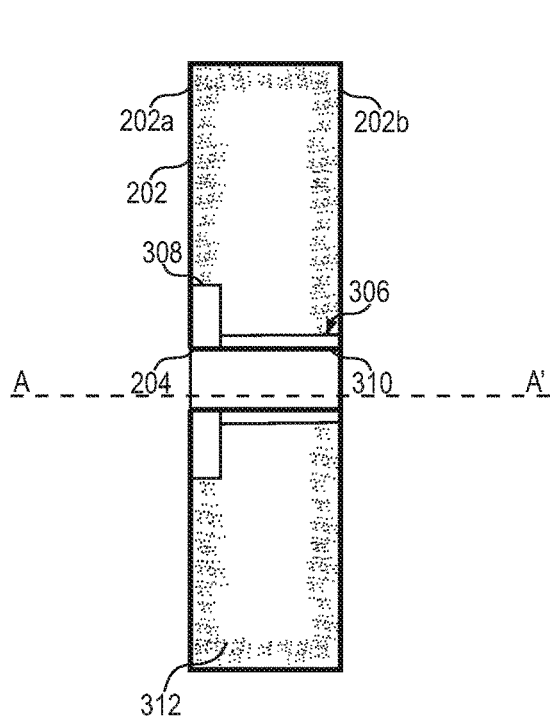
FIG. 3A is a sectional side view of the disposable endoscope shield including a coupling member, in accordance with an exemplary embodiment of the present disclosure.
Figure 3B:
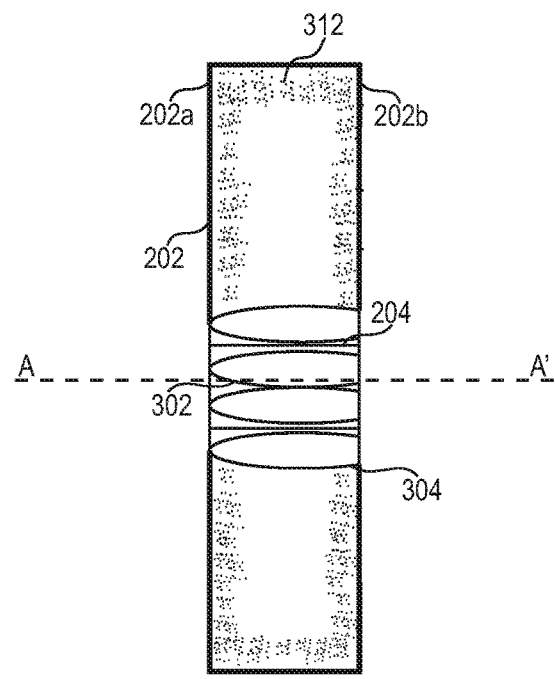
FIG. 3B is a sectional side view of the disposable endoscope shield, illustrating a bite-block, in accordance with an exemplary embodiment of the present disclosure.

Referring now to FIGS. 3A and 3B, the opening 204 also includes a coupling mechanism 302, configured for engaging the outer surface of the endoscope 106 (for e.g. as shown in FIG. 1). The coupling mechanism 302, on engagement with the endoscope 106, establishes the interference fit, thereby reinforcing the coupling between the opening 204 and the endoscope 106. The coupling mechanism 302 is configured around the perimeter of the opening 204, for ease of coupling with the endoscope 106. In one configuration, the coupling mechanism 302 is configured with a plurality of petals 304 around the periphery of the opening 202. The plurality of petals 304 extends from the second surface 202b towards the first surface 202a along the axis A-A'. The plurality of petals 304 engage onto the outer surface of the endoscope 106 upon insertion into the opening 202, such that the opening is relatively closed with respect to the endoscope 106. This configuration, therefore, ensures freedom of movement for the endoscope 106 upon insertion into the opening 204, while also preventing majority of the effluents from splattering onto the user 114. In another embodiment, the coupling mechanism 302 may be an elastic member or a stretchable member (not shown in Figures) configured around the opening 204. The elastic member may relatively engage onto the outer surface of the endoscope 106, without compromising maneuverability of the endoscope 106, while also preventing fluids splattering on the user 114. The coupling mechanism 302 is configured such that, the outer surface of the endoscope 106 experiences negligible deformation due to the coupling force or the clamping force exerted on the endoscope 106 upon coupling. Thus, the coupling mechanism 302 also acts as a bite-block for the endoscope 106.

In an embodiment, a bite-block member 306 (for e.g. as shown in FIG. 3B) may be configured to the opening 204, along with the coupling mechanism 302 for preventing damage to the endoscope 106 during use. The bite-block member 306 includes a casing 308 mountable on the second surface 202b and includes a cylindrical tube 310 laterally extending from the casing 308. The cylindrical tube 310 is configured such that, its inner diameter is identical to the opening 204. Also, the casing 308 is positioned such that the cylindrical tube 310 is aligned coaxially to the opening 204. The cylindrical tube 310 provides the required support to the endoscope 106 during use, while also preventing damage to the endoscope 106 during use. The bite-block member 306 may be manufactured from materials conventionally used in the industry i.e. with sufficient stiffness for preventing damage to the endoscope 106. In an embodiment, the cylindrical tube 310 may be oriented towards the subject 102, while also protruding away from the first surface 102 (not shown in Figures). This configuration may enable the user 114 to insert a portion of the cylindrical tube 310 within the cavity 108. This feature prevents damage to the endoscope 106 upon insertion into the internal organ 110.

Figure 4:
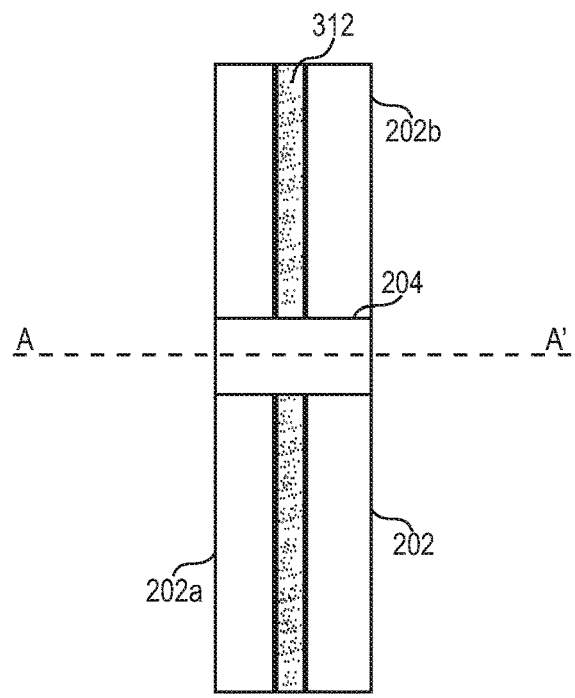
FIG. 4 is a sectional side view of the disposable endoscope shield including a fluid protection layer, in accordance with an exemplary embodiment of the present disclosure.

Further, the shield body member 202 comprises a fluid protection layer 312. The fluid protection layer 312 is positioned between the first surface 202a and the second surface 202b and configured to protect the user 114 from splattering of fluids from the subject 102 during the endoscopy. In one configuration, the fluid protection layer 312 may be integrally formed in the body member 202 (as shown in FIG. 3A) between the first surface 202a and the second surface 202b. In another configuration, the fluid protection layer 312 may be inserted or positioned between the first surface 202a and the second surface 202b (for e.g. as shown in FIG. 4) forming, a sandwich construction. As such, the body member 202 may be configured with a construction capable of receiving the fluid protection layer 312. In one embodiment, the body member 202 may be made by joining of separate layers, while also introducing the fluid protection layer 312 therebetween. Further, the fluid protection layer 312 may be configured to absorb the fluids splattering from the internal organ 110 (for e.g. as shown in FIG. 1) for protecting the user 114. As such, the fluid protection layer 312 may be made of an absorbent material such as but not limited to cellulose, SAP or superabsorbent polymers, hydrogel, sodium plycrylde, charcoal or any other material as per feasibility and requirement. In another configuration, the fluid protection layer 312 is impervious to fluids and therefore blocks the flow of fluids splattering from the internal organ 110. As such the fluid protection layer 312 is made of materials which are impervious to the fluids. The impervious material may be selected from one of a bioplastic material, a plastic material, a petroleum based impervious material, a polyurethane material, a plastic treated material, a jute treated material, a cloth and the like as per feasibility and requirement. In an embodiment, the fluid protection layer 312 may extend radially from the opening 204. The dimension of the radial extension may be selected as per design feasibility and requirement.

Figure 5A:
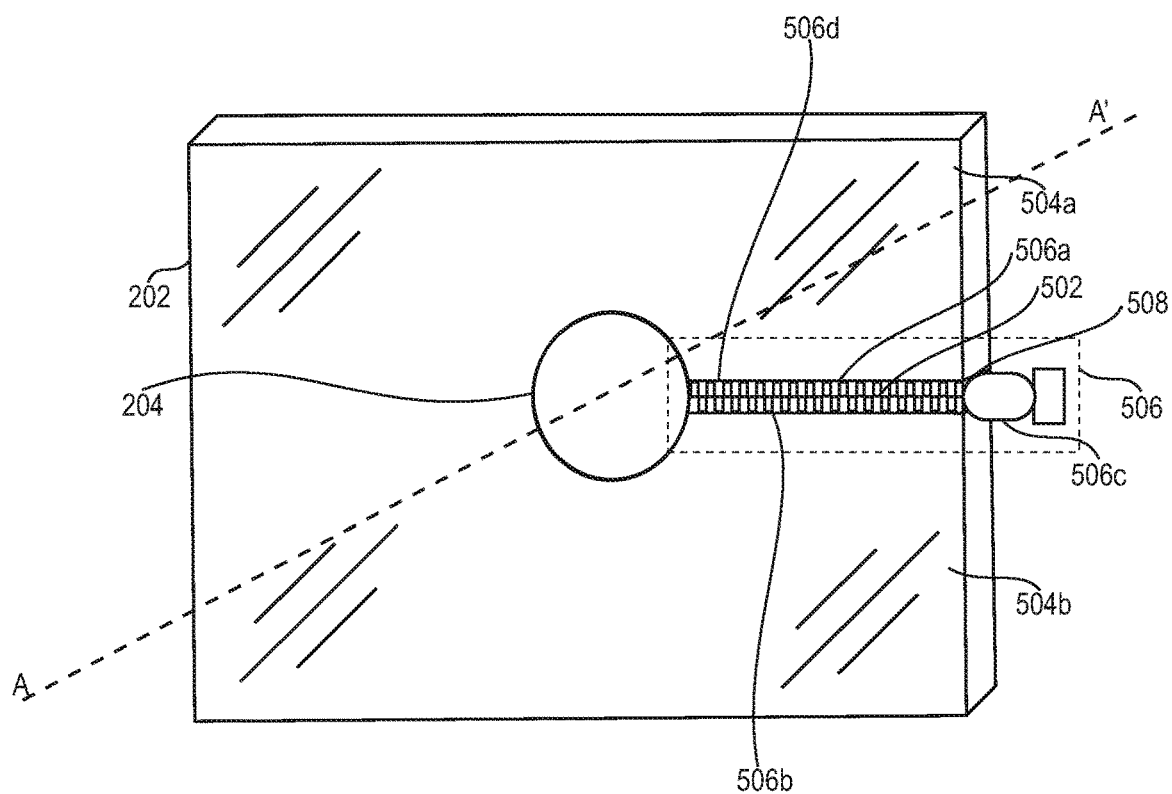
FIG. 5A is a schematic view of the disposable endoscope shield including a slit and a fastening mechanism, in accordance with an exemplary embodiment of the present disclosure.
Figure 5B:
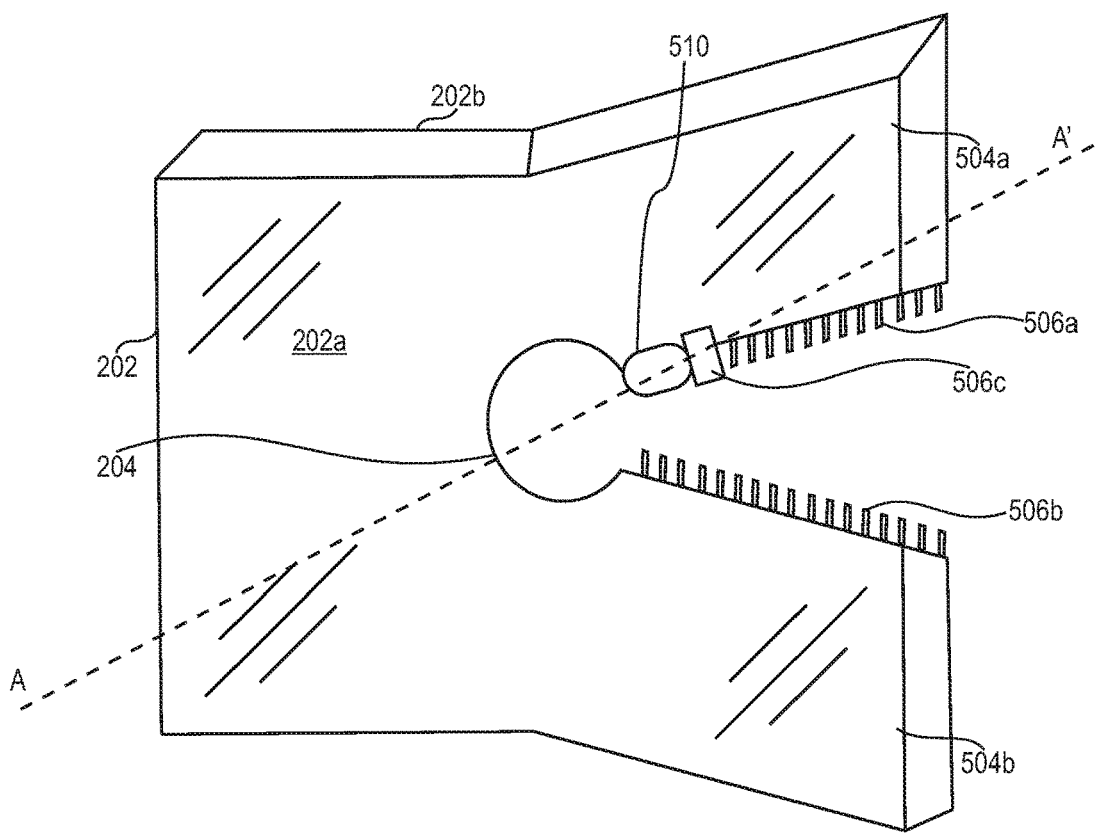
FIG. 5B is a schematic view of the disposable endoscope shield including the slit and the fastening mechanism, in accordance with another embodiment of the present disclosure.

FIGS. 5A and 5B in one exemplary embodiment of the present disclosure illustrate the shield 100 configured with a slit 502. The slit 502 extends from the opening 204 or from a margin of the opening 204 and up to the outer surface or periphery of the body member 202. In one configuration, the slit 502 extends laterally to the axis A-A' of the body member 202 up to the outer surface of the body member 202. The slit 502 is configured to split the body member 202 to a first portion 504a and a second portion 504b, for enabling the user 114 to wrap the body member 202 around the endoscope 106. This feature facilitates the user 114 to either insert a new shield 100 or replace a foiled shield 100 around the endoscope 106, without the need for removing the endoscope 106 from the internal organ 110. This configuration enhances hygiene while also reducing trauma to the subject 102 due to the removal and re-insertion of the endoscope 106. As an example, FIGS. 5A and 5B illustrate a part of the body member 202 (i.e. half of the body member 202) being split due to the slit 502. Therefore, it is apparent that the size and configuration of the slit 502 may vary based on the configuration of the body member 202 or as per user 114 requirement.

Figure 6A:
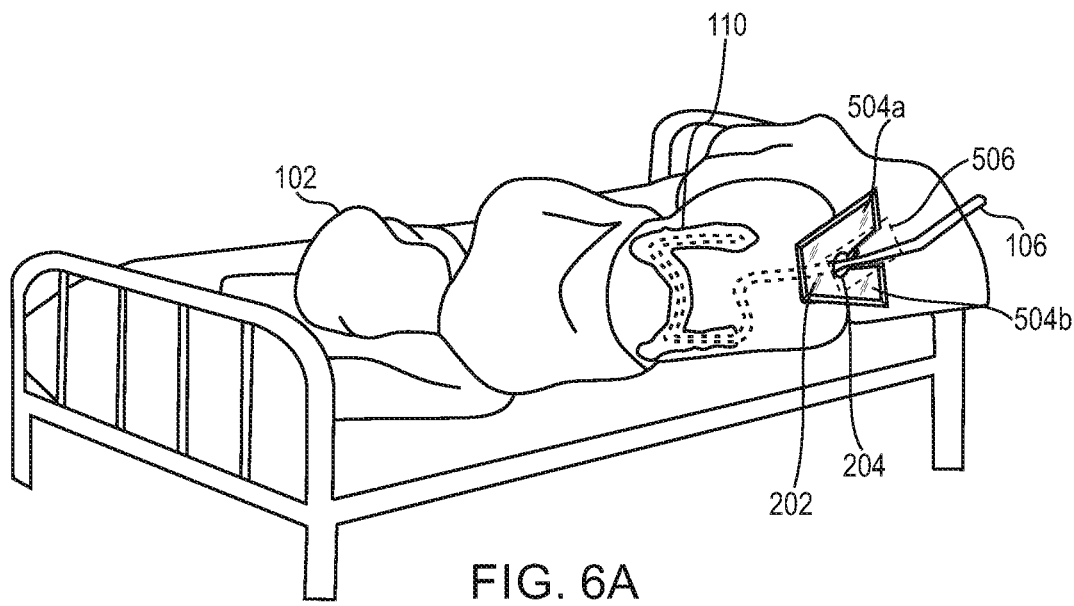
FIG. 6A is a schematic view of the disposable endoscope shield being wrapped around the endoscope, in accordance with an exemplary embodiment of the present disclosure.
Figure 6B:
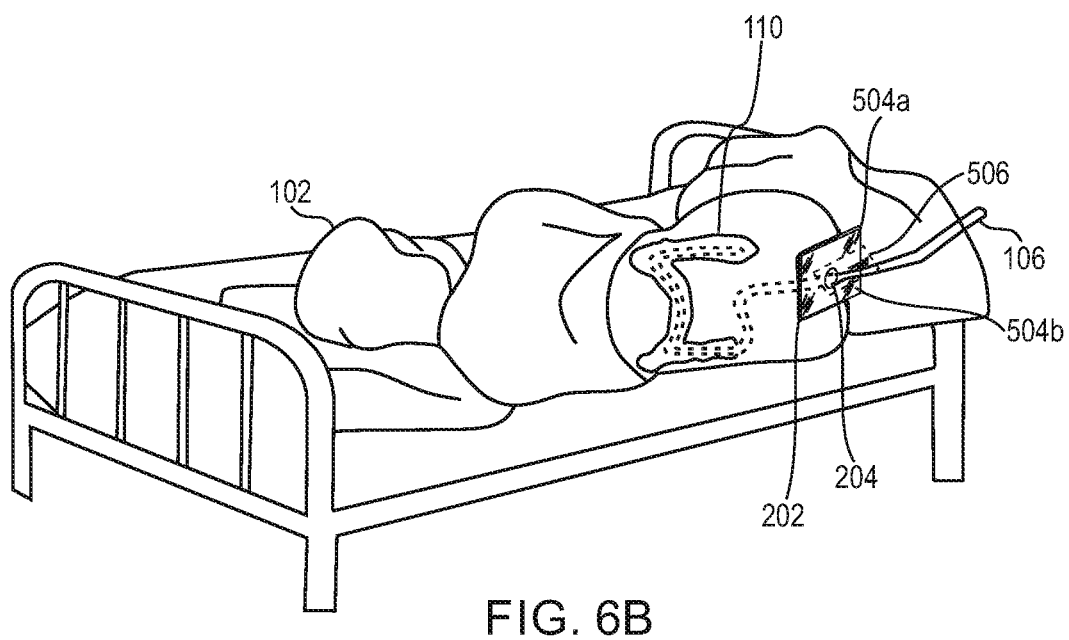
FIG. 6B is a schematic view of the disposable endoscope shield wrapped around endoscope, in accordance with an exemplary embodiment of the present disclosure.

The slit 502 is configured with a fastening mechanism 506. The fastening mechanism 506 is configured to be operable in an engaged position 508 and a disengaged position 510, for opening and closing the slit 502, thereby providing versatility to the user 114 for replacing or removing the shield 100 from the treatment area. 506. In the engaged position 508, the fastening member 506 interlocks the first portion 504a with the second portion 504b of the body member 202 forming a unitary structure, thereby closing the slit 502. In the disengaged position 510, the slit 502 is opened and thereby the body member 202 is divided into the first portion 504a and the second portion 504b. The splitting of the body member 202 facilitates the user 114 to manipulate the first portion 504a and the second portion 504b suitably, for wrapping the body member 202 around the endoscope 106 (for e.g. as shown in FIGS. 6A and 6B).

In one configuration, the fastening mechanism 506 is a zipper mechanism, which operates similar to the conventional zippers. The zipper mechanism 506 may include a first rail 506a connected to the first portion 504a and a second rail 506b connected to the second portion 504b of the body member 202. The first rail 506a and the second rail 506b are configured with a plurality of teeth 506d along their lengths, which can engage with each other to form a coupling. A slider 506c may be incorporated on the first rail 506a and configured to slide along the length of the first rail 506a from the engaged position 508 to the disengaged position 510. In the engaged position 508, the slider 506c is located at the perimeter of the body member 202 and in the disengaged position 510 the slider 506c is located proximal to the opening 204. For coupling the first portion 504a and the second portion 504b, the slider 506c in the disengaged position 510 is engaged with the second rail 506b and thereupon slid along the length of the first rail 506a. In this juncture, the plurality of teeth 506d of the first rail 506a and the second rail 506b engage with each other, while the slider 506c is moving to the engaged position 508, thereby coupling the first portion 504a with the second portion 504b. For splitting the first portion 504a and the second portion 504b, the slider 506c in the engaged position 508 is moved towards the opening 204. At this juncture, the slider 506c decouples the first rail 506a and the second rail 506 during its movement towards the opening 204. At the disengaging position 510, the slider 506c completely disengages from the second rail 506b, thereby splitting the first portion 504a and the second portion 504b.

In one implementation, the configuration of the fastening mechanism 506 may be suitably interchanged without deviating from the scope of the present disclosure. In other words, the slider 506c may also be mounted on the second rail 506b and configured to slide along the length of the second rail 506b from the engaged position 508 to the disengaged position 510. In the engaged position 508, the slider 506c is located at the vicinity of the opening 204 and in the disengaged position 510 the slider 506c is located at the perimeter or the outer surface of the body member 202. For coupling the first portion 504a and the second portion 504b, the slider 506c in the disengaged position 510 is engaged with the first rail 506a and thereupon slid along the length of the second rail 506b towards the opening 204. For splitting the first portion 504a and the second portion 504b in this configuration, the slider 506c in the engaged position 508 is moved towards the outer surface.

Figure 5C:
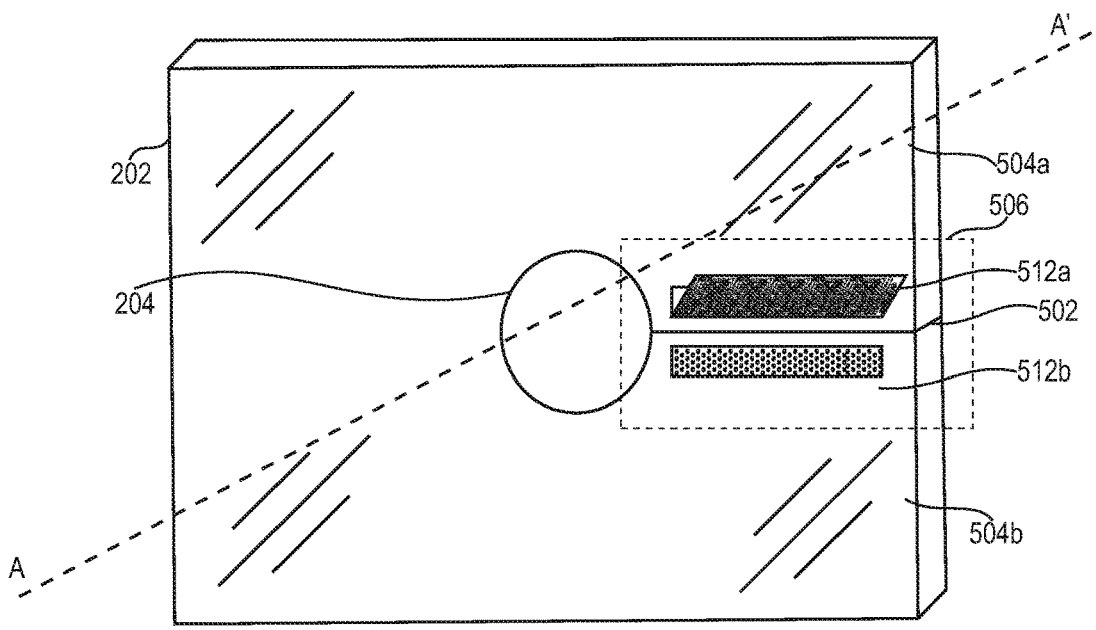
FIG. 5C is a schematic view of the disposable endoscope shield including the fastening mechanism, in accordance with another embodiment of the present disclosure.

Referring to FIG. 5C in conjunction with FIGS. 5A and 5B, the fastening mechanism 506 is configured to be a Velcro™-strap mechanism. The fastening mechanism 506 includes a male connector 512a connected to the first portion 504a and a female connector 512b connected to the second portion 504b. The male connector 512a engages with the female connector 512b in the engaged position 508, for interlocking the first portion 504a and the second portion 504b. Similarly, the male connector 512a disengages with the female connector 512b in the disengaged position 510 for splitting the body member 202. In one configuration, the male connector 512a may be a strap member and the female connector 512b may be a Velcro™ The male connector 512a and the female connector 512b may extend along the length of the slit 502, for ensuring snug fit configuration of the body member 202 on the endoscope 106 upon coupling. Alternatively, the male connector 512a and the female connector 512b may extend to lengths as per design feasibility and requirement. In the engaged position 508, the strap member 512a engages with the Velcro™ 512b, thereby coupling with each other. In the disengaged position 510, the strap member 512a disengages with the Velcro™ 512b, thereby splitting the body portion 202.

In one configuration, the fastening mechanism 506 is configured to be a snap-fit mechanism (not shown in Figures). In this configuration, the fastening mechanism 506 the male connector 512a is a pin member and the female connector 512b is a groove member configured to receive the pin member. In the engaged position, the pin member engages with a groove in a snap-fit configuration for coupling. In the disengaged position 510, the pin member disengages with the groove.

In an embodiment, the fastening mechanism 506 is manufactured by medical grade materials, for use on the subject 102 during the endoscopy.

FIGS. 6A and 6B in one exemplary embodiment of the present disclosure illustrate placement or insertion of the shield 100 on the treatment area, while the endoscope 106 is in use. When the shield 100 is foiled or is required to cover the treatment are or to be attached on to the subject 102 upon insertion of the endoscope 106, the fastening mechanism 506 is operated to the disengaged position 510 for splitting the body member 202 into the first portion 504a and the second portion 504b. This feature facilitates the user 114 to manipulate the body member 202 accordingly, for wrapping around the endoscope 106 (as shown in FIG. 6A). Once the body member 202 is suitably located and aligned, the fastening member 506 is operated to the engaged position 508 for interlocking the body member 202, thereby locking the shield 100 onto the endoscope 106 which is already in use (as shown in FIG. 6A). Once the body member 202 is locked, the user 114 may attach the first surface 202a (as shown in FIG. 2) on to the treatment area or may cover the treatment area via the first surface 202a, thereby protecting the user 114 from fluids splattering.

Figure 7:
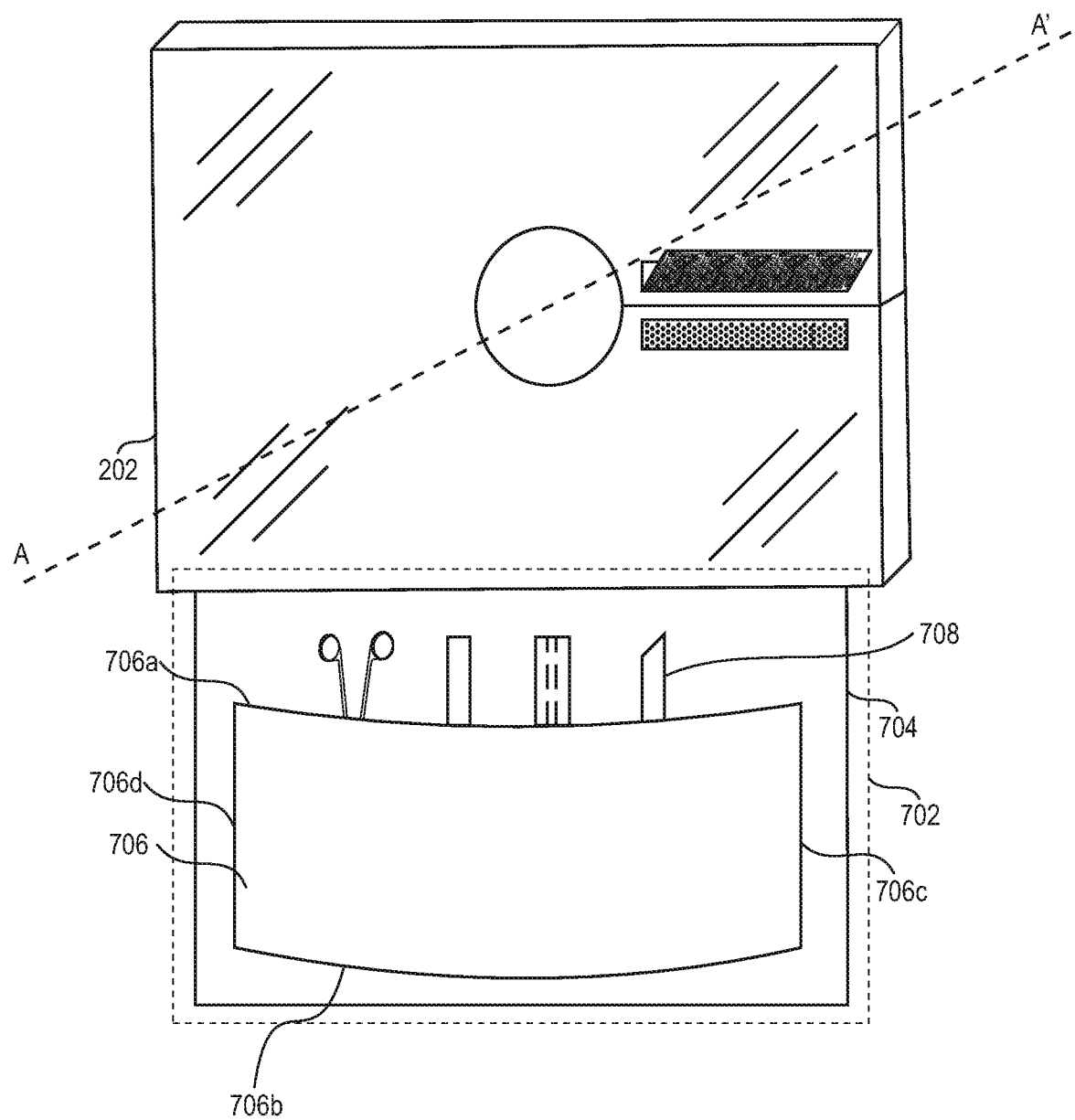
FIG. 7 is a schematic view of the disposable endoscope shield including a pocket member, in accordance with an exemplary embodiment of the present disclosure.

FIG. 7 in one exemplary embodiment of the present disclosure illustrates the shield 100 configured with a pocket member 702. The pocket member 702 may be configured to the body member 202 for storing accessories 708 required for performing the endoscopy. In one configuration, the pocket member 702 is attached to the body member 202, by conventional techniques such as adhesive bonding, fastening and the like. In another configuration, the pocket member 702 may be integrally formed or may extend from the body member 202. The pocket member 702 may include a base panel 704 configured on the body member 202. The base panel 704 includes a support panel 706, which is configured as a pocket for storing the accessories 708. The support panel 706 includes a top end 706a, a bottom end 706b, a side ends 706c and 706d. The support panel 706 may be configured on the base panel 704 such that, the bottom end 706b and the side ends 706c, 706d are fixed onto the base panel 704, while the top end 706a is free or unrestricted. This configuration of the support panel 706 acts as a storage compartment for the accessories 708. Alternatively, the ends of the support panel 706 may be suitably re-arranged for altering the configuration of the support panel 706 on the base panel 704, thereby altering the configuration of the pocket member 702. In one configuration, the right-side end 706c is open while other ends of the support panel 706 are closed (not shown in Figures). The configuration of the pocket member 702 is selected based on the accessories 708 that are required to be stored therein. The accessories 708 may include, operative instruments, gauzes or any other medical accessories required for performing the endoscopy. Further, the pocket member 702 may also include a cap member (not shown in Figures) located above the top end 706a, for containing the accessories 708 within the pocket member 702. The pocket member 702 may be preferably manufactured with materials identical to that of the body member 202, i.e. the medical grade materials.

Figure 8:
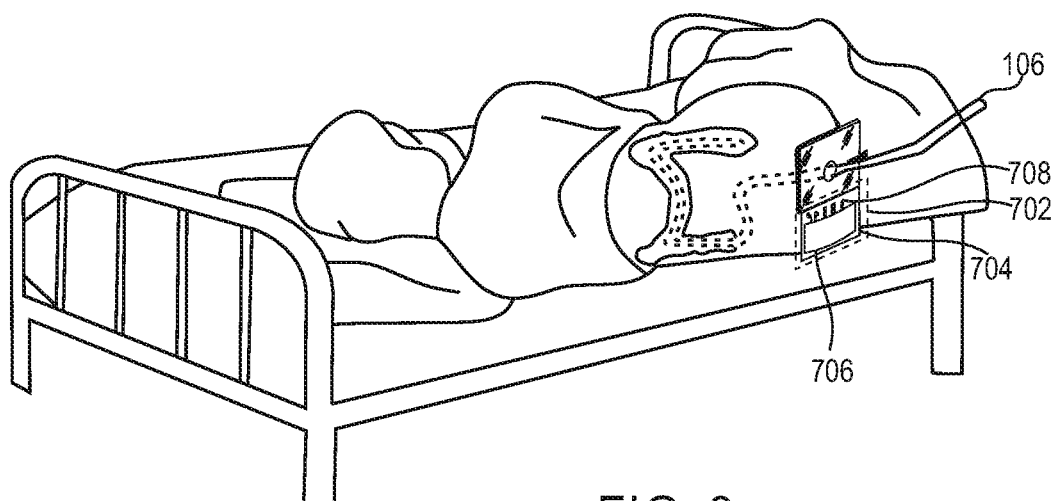
FIG. 8 is a schematic view of the disposable endoscope shield covered on the subject along with the pocket member, in accordance with an exemplary embodiment of the present disclosure.

FIG. 8 in one exemplary embodiment of the present disclosure, illustrates the shield 100 along with the pocket member 702 attached to the subject 102. The shield 100 may cover the treatment area or may be attached to the subject 102 before commencement or initiating the endoscopy (as described in the description of FIG. 2) or after initiation of the endoscopy (as described in the description of FIGS. 6A and 6B). Accordingly, the pocket member 702 may be attached to the shield 100 by suitable fastening means. As such, the body member 202 is configured with a fastening means (not shown in Figures) for receiving and fastening the pocket member 702. This configuration enhances flexibility to the user 114 for attaching the pocket member 702 as and when required. This configuration also provides versatility to the user 114 to alter the orientation of the pocket member 702 as per user 114 requirement. In another configuration, the shield 100 which is covering the treatment area or attached to the subject 102 may already be configured with the pocket member 702. In other words, the pocket member 702 may be integrally formed with the shield 100. The pocket member 702 may be oriented suitably for facilitating the use of accessories 708 by the user 114 during endoscopy.

Figure 9:
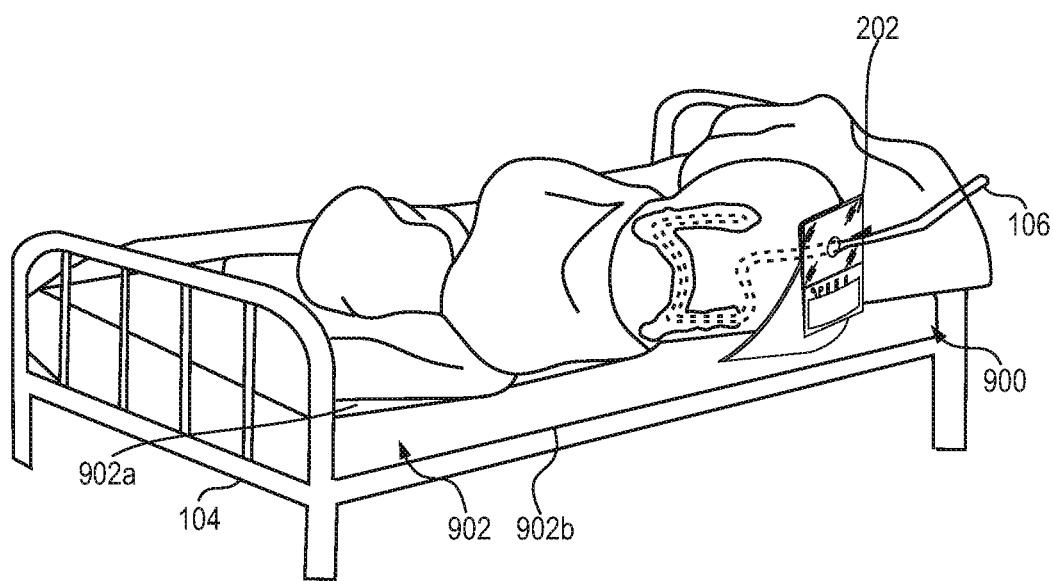
FIG. 9 is a schematic view of a medical procedure mat including the disposable endoscope shield, in accordance with an exemplary embodiment of the present disclosure.

FIG. 9 in one exemplary embodiment of the present disclosure, illustrates a medical procedure mat 900 configured with the shield 100. The medical procedure mat 900 includes a cushion member 902 which provides comfort to the subject 102 during the use of the mat 900. The mat 900 is further configured with the shield 100 with the configuration as already described. The shield 100 may either be fastened to the mat 900 or may be integrally manufactured (similar to the pocket member 702). This configuration mitigates the need for carrying separate shield 100 for the subject 102, as the shield 100 is made readily available in the mat 900. Further, the cushion member 902 may be made of materials used in conventional cushions of the medical procedure tables 104.

In an embodiment, the shield 100 may also be incorporated in surgical drapes (not shown in Figures) which are worn by the subject 102 prior to medical treatment. The shield 100 may be configured to the surgical drape similarly as configured in the case of the mat 900.

In one embodiment the opening 204 of the shield 100, through which the endoscope 106 will be pushed in or pulled out may reside on a flap which could be attached to the surgical drape (not shown in Figures). Once the surgical drape is put in position on top of the medical procedure mat 900, the flap will be retracted, for full exposure of the treatment area for prior examination. Thereafter, the flap would be covered on the treatment area for insertion of the endoscope 106 to perform the endoscopy. As an example, in colonoscopy, upon retracting the flap, the user 114 will perform a digital exam (as is customary before inserting scope) and then the flap will be flipped back to cover the buttocks area. Thereafter, the endoscope is inserted for endoscopy. In another implementation, for Esophagogastroduodenoscopy (EGD) procedure, the surgical drape may be put on top of a pillow below a head and neck area of the subject 102 and bite-block 306 is inserted onto a mouth of the subject 102 (not shown in the Figures). Once the subject 102 is unconscious upon administering anesthesia, the flap will be retracted back from the surgical drape and will be put over a face of the subject 102. In this configuration, the opening 204 will be aligned with the cylindrical tube 310 of the bite-block 306 for enabling the subject 102 to insert the endoscope for conducting the endoscopy.

The benefits and advantages described above may relate to one embodiment or may relate to several embodiments. The embodiments are not limited to those that solve any or all of the stated problems or those that have any or all of the stated benefits and advantages.

The above description is given by way of example only and various modifications may be made by those skilled in the art. The above specification, examples, and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification.

What is claimed is:

1. A disposable endoscope shield, comprising:
a shield body member including a first surface and a second surface, the first surface configured to cover a treatment area of a subject and the second surface oriented towards a user of an endoscope device,
wherein the shield body member is configured with an opening extending from the first surface to the second surface, for allowing the endoscope device to access an internal organ of the subject via a cavity, for performing an endoscopy, and
wherein the shield body member comprises a fluid protection layer configured between the first surface and the second surface of the shield body member, for protecting the user from fluids splattering from the internal organ of the subject during the endoscopy, and wherein the fluid protection layer is positioned between the first surface and the second surface, forming a sandwich construction;
a coupling member configured around a perimeter of the opening and positioned parallelly about an axis of the opening for engaging with the endoscope device, wherein the coupling member extends from the second surface towards the first surface and sealingly couples with the endoscope device upon insertion into the opening; and
a bite-block configured between the first surface and the second surface and aligned coaxially with the opening, the bite-block comprising a casing mountable on the second surface and a cylindrical tube laterally extending from the casing, the bite-block configured to prevent damage to the endoscope device upon insertion into the internal organ.

2. The disposable endoscope shield as claimed in claim 1, wherein the first surface is configured with a biocompatible adhesive for covering the treatment area of the subject via the shield body member.

3. The disposable endoscope shield as claimed in claim 1, further comprising a pocket member configured to the shield body member for storing accessories required for the endoscopy.

4. The disposable endoscope shield as claimed in claim 1, wherein the shield body member is configured to a medical procedure mat.

5. The disposable endoscope shield as claimed in claim 1, wherein the fluid protection layer is configured to absorb the fluids splattering from the internal organ during the endoscopy, for protecting the user.

6. The disposable endoscope shield as claimed in claim 1, wherein the fluid protection layer is configured to be impervious to the fluids splattering from the internal organ, for protecting the user.

7. The disposable endoscope shield as claimed in claim 1, further comprising a slit extending from the opening to an outer surface of the shield body member, the slit configured with a fastening mechanism operable to an engaged position in which the slit is closed, and to a disengaged position in which the slit is open.

8. The disposable endoscope shield as claimed in claim 7, wherein:
in the disengaged position of the fastening mechanism, the shield body member is split into a first portion and a second portion and allowing the user to wrap the shield body member around the endoscope device inserted within the internal organ, such that the opening encircles the endoscope device; and
in the engaged position of the fastening mechanism, the first portion is interlocked with the second portion to form a unitary structure of the shield body member.

9. A disposable endoscope shield, comprising:
a shield body member comprising a first surface and a second surface, the first surface configured to cover a treatment area of a subject and the second surface oriented towards a user of an endoscope device,
wherein the shield body member is configured with an opening extending from the first surface to the second surface, for allowing the endoscope device to access an internal organ of the subject via a cavity, for performing an endoscopy;
a coupling member configured around a perimeter of the opening and positioned parallelly about an axis of the opening for engaging with the endoscope device, wherein the coupling member extends from the second surface towards the first surface and sealingly couples with the endoscope device upon insertion into the opening;
a fluid protection layer configured between the first surface and the second surface, for preventing splashing of fluids onto the user from the subject during the endoscopy, and wherein the fluid protection layer is positioned between the first surface and the second surface, forming a sandwich construction;
a pocket member configured to the shield body member, for storing accessories required for the endoscopy; and
a bite-block configured between the first surface and the second surface and aligned coaxially with the opening, the bite-block comprising a casing mountable on the second surface and a cylindrical tube laterally extending from the casing, the bite-block configured to prevent damage to the endoscope device upon insertion into the internal organ.

10. The disposable endoscope shield as claimed in claim 9, wherein the first surface is configured with a biocompatible adhesive for covering the treatment area of the subject via the shield body member.

11. The disposable endoscope shield as claimed in claim 9, wherein the shield body member is a medical procedure mat.

12. The disposable endoscope shield as claimed in claim 9, wherein the fluid protection layer is configured to absorb the fluids splattering from the internal organ during the endoscopy, for protecting the user.

13. The disposable endoscope shield as claimed in claim 9, wherein the fluid protection layer is configured to be impervious to the fluids splattering from the internal organ, for protecting the user.

14. The disposable endoscope shield as claimed in claim 9, further comprising a slit extending from the opening to an outer surface of the shield body member, the slit configured with a fastening mechanism operable to an engaged position in which the slit is closed, and to a disengaged position in which the slit is open.

15. The disposable endoscope shield as claimed in claim 14, wherein
in the disengaged position of the fastening mechanism, the shield body member is split into a first portion and a second portion and allowing the user to wrap the shield body member around the endoscope device inserted within the internal organ, such that the opening encircles the endoscope device; and
in the engaged position of the fastening mechanism, the first portion is interlocked with the second portion to form a unitary structure of the shield body member.

16. A medical procedure mat, comprising:
a cushion member; and
a disposable endoscope shield configured to the cushion member, the disposable endoscope shield comprising:
a shield body member comprising a first surface and a second surface, the first surface configured with a biocompatible adhesive for covering a treatment area of a subject via the shield body member and the second surface oriented towards a user of an endoscope device,
wherein the shield body member is configured with an opening extending from the first surface to the second surface, for allowing the endoscope device to access an internal organ of the subject via a cavity, for performing an endoscopy,
wherein, a slit extending from the opening to an outer surface of the shield body member, the slit configured with a fastening mechanism operable to an engaged position in which the slit is closed, and to a disengaged position in which the slit is open,
wherein in the disengaged position of the fastening mechanism, the shield body member is split into a first portion and a second portion and allowing the user to wrap the shield body member around the endoscope device inserted within the internal organ, such that the opening encircles the endoscope device, and
wherein in the engaged position of the fastening mechanism, the first portion is interlocked with the second portion to form a unitary structure of the shield body member;
a coupling member configured around a perimeter of the opening and oriented parallelly about an axis of the opening for engaging with the endoscope device, wherein the coupling member extends from the second surface towards the first surface and sealingly couples with the endoscope device for protecting the user during the endoscopy;
a fluid protection layer configured between the first surface and the second surface, for preventing splashing of fluids onto the user from the subject during the endoscopy, and wherein the fluid protection layer is positioned between the first surface and the second surface, forming a sandwich construction;
a pocket member configured to the shield body member, for storing accessories required for the endoscopy; and a bite-block configured between the first surface and the second surface and aligned coaxially with the opening, the bite-block comprising a casing mountable on the second surface and a cylindrical tube laterally extending from the casing, the bite-block configured to prevent damage to the endoscope device upon insertion into the internal organ.

17. The disposable endoscope shield as claimed in claim 1, wherein the fluid protection layer is made of an absorbent material comprising one or more of: superabsorbent polymer, hydrogel, sodium plycrylde, and charcoal.

\* \* \* \* \*